United States Patent [19]
Drauz et al.

[11] Patent Number: 6,090,913
[45] Date of Patent: *Jul. 18, 2000

[54] TRANSESTERIFICATION AND OTHER CONVERSION REACTIONS OF ACID DERIVATIVES, USING AN AMIDINE BASE

[75] Inventors: Karlheinz Drauz, Freigericht; Thomas Müller, Frankfurt; Matthias Kottenhahn, Freigericht, all of Germany; Dieter Seebach, Zürich; Adrian Thaler, Steinhausen, both of Switzerland

[73] Assignee: Degussa-Huls Aktiengesellschaft, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/826,258

[22] Filed: Mar. 27, 1997

Related U.S. Application Data

[63] Continuation of application No. 08/438,187, May 12, 1995, abandoned, which is a continuation-in-part of application No. 07/913,459, Jul. 15, 1992, abandoned.

[30] Foreign Application Priority Data

Jul. 15, 1991 [DE] Germany .............................. 41 23 408
Jul. 22, 1991 [DE] Germany .............................. 41 24 283

[51] Int. Cl.$^7$ .............................. C07C 67/02; C07K 1/12
[52] U.S. Cl. .......................... 530/338; 530/343; 530/345; 560/19; 560/155
[58] Field of Search ...................... 530/334, 338, 530/343, 345; 560/19, 155

[56] References Cited

U.S. PATENT DOCUMENTS

| | | | |
|---|---|---|---|
| 4,350,627 | 9/1982 | De Castiglione et al. | 260/112.5 |
| 4,692,506 | 9/1987 | Yatsu et al. | 528/296 |
| 4,876,378 | 10/1989 | Van Sickle | 560/78 |
| 5,015,753 | 5/1991 | Harris | 558/260 |

FOREIGN PATENT DOCUMENTS 110629  6/1984  European Pat. Off. .

OTHER PUBLICATIONS

Seiwell, L.P., "Copper–Catalyzed Nonaqueous Ammonolysis of p–Chlorobenzotrifluoride. Effect of Potassium Fluoride.", J. Org. Chem., vol. 44, No. 25, pp. 4731–4733, 1979.

Chen et al., "Side Reaction in Peptide Synthesis", Int. J. Peptide Protein Research, vol. 35. pp. 52–54, 1990.

Miranda et al., "Transesterification of Peptide Esters and Peptidyl Resin in Methanol–Containing Calcium Acetate", Int. J. Peptide Protein Res., vol. 37, pp. 451–456, Apr. 1991.

Andrea et al., "A Compartive Study of the 'Sopanification Strength' of Alkaline Bases: Potassium, Sodium, and Lithium Hydroxides", Olegineux, vol. 21, No. 11, pp. 687–689. (Abstract Only), 1966.

Yasutome et al., "Sopanification Treatment. 1. Saponificatin in Yarin Style, Sen 'I Kako", vol. 33, No. 7, pp. 336–339 (Abstract Only), 1981.

Carey, F.A., Organic Chemistry, McGraw–Hill, New York, pp. 793–798, 1987.

N.N. Greenwood and A. Earnshaw, Chemistry of the Elements, Pergamon Press, Oxford, pp. 87.

F.A. Cotton and Geoffrey Wilkinson, Advanced Inorganic Chemistry, John Wiley & Sons, New York, p. 253.

*Primary Examiner*—Michael P. Woodward
*Assistant Examiner*—Anish Gupta
*Attorney, Agent, or Firm*—Cushman Darby & Cushman IP Group of Pillsbury Madison & Sutro

[57] ABSTRACT

A process employs amidine or amidine base and a metal compound in the presence of an alcohol or water to transesterify, or saponify esters or amides. Since the process employs relatively mild conditions, it is especially suitable for the production of optically active substances and biomolecules, e.g. peptides, amino acids and nucleic acids which are sensitive to elevated temperatures, extreme pH values and/or long reaction times since these compounds are easily racemised or denatured. The conditions additionally find use in solid phase systems. When amino acid or peptide esters are saponified, the splitting is brought about with lithium hydroxide alone under mild conditions. The use of an amidine base, more particularly DBU or DBN, in combination with the metal salt additionally accelerates the reaction so strongly that even sensitive acid derivatives can be reacted under mild conditions. The amidine based system lends itself to the manufacture of complex esters, gentle splitting of peptides from the carrier, gentle saponification of amides or esters.

12 Claims, No Drawings

TRANSESTERIFICATION AND OTHER CONVERSION REACTIONS OF ACID DERIVATIVES, USING AN AMIDINE BASE

This is a continuation of application Ser. No. 08/438,187, filed on May 12, 1995, which was abandoned upon the filing hereof, which is a continuation-in-part of application Ser. No. 07/913,459, filed Jul. 15, 1992, now abandoned.

BACKGROUND OF THE INVENTION

1. Field of the Invention

The invention relates to a method of reacting a phosphoric acid, phosphonic acid or carboxylic acid derivative with an alcohol, water or $NH_3$ in the presence of an amidine base, more particularly a method of transesterification, ammonolysis or saponification of carboxylic acid, phosphonic acid or phosphoric acid derivatives and splitting of amino acid, peptide or nucleic acid derivatives from a polymer carrier. The invention also relates to a method of saponifying a peptide ester in an aqueous medium in the presence of a base in the form of a metal compound.

2. Background Information

Various methods of transesterifyinq or saponifying the aforementioned compounds are already described in the literature. Operation is e.g. under strongly acid or basic conditions, with enzymes (D. Seebach, Angew. Chem. 1990, 102, 1363), with titanates (D. Seebach, B. Weidmann, L. Widler in "Modern Synthetic Methods", 1983), or KF/cyclic ethers (B. Lejczak, P. Kafarski, J. Szewczyk, Synthesis 1982, 412) or with ion exchange resins (W. Pereira, V. Close, W. Patton, B. Halpfern, J. Org. Chem. 1969, 34, 2032) or distannic oxanes (J. Otera, S. Ioka, H. Nozaki, J. Org. Chem. 1989, 5*, 4013). There is also a description of a method of transesterifying or saponifying ester derivatives using the amidine base DBU in solution (EP 0 110 629 and 0 150 962) or polymer-bonded (T. Ishikawa, Y. Ohsumi, T. Kawai, Bull. Chem. Soc. Jpn. 1990, 63, 819).

EP 0 110 629 Al discloses use of amidine bases for transesterification. The amidine is usually supported by epoxides. The citation does not mention particularly mild conditions, as necessary particularly when reacting optically active biomolecules. All the examples describe simple stable compounds without additional functional groups or optical activity.

Transesterification using calcium acetate in methanol is known from Int. J. Peptide Protein Res. 37, 1991, 451–456. In the great majority of cases, the substrates are only peptides with a C-terminal glycine radical. These peptides are insensitive to racemisation. When a C-terminal alanyl radical is used, the reaction is already inhibited. Also, this reaction requires specific protective groups. A universally applicable mild method, more particularly for reacting biomolecules, cannot be obtained by using calcium acetate.

The splitting of carboxylic acid methyl esters with DBU at 165° C. in 48 hours is known from J. Org. Chem. 38, (1973), 1223–1225. These conditions are too drastic for most ester splitting, particularly for optically active esters having a center of chirality in the α position relative to the ester group.

β-elimination with DBU or DBN is known from CA 114, 186011 (1991) and Tetrahedron Letters 21 (1980), 1181–1184. As is universally the case in β-elimination and also mentioned in this citation, theoretically any base, even potassium hydroxide, can be used. The citation does not describe universally applicable mild reaction conditions.

All the previously-mentioned methods, except for the enzymatic method, normally require elevated temperatures, extreme pH values and/or long reaction times. Owing to the reaction conditions, most of the aforementioned methods are unsuitable for sensitive ester derivatives, e.g. containing additional functional groups or one or more chiral C atoms, more particularly compounds containing a chiral C atom in the α position relative to the ester function.

SUMMARY OF THE INVENTION

The invention therefore is concerned with a system for reaction, more particularly saponification, ammonolysis or transesterification, of acid derivatives and splitting of polymer-bonded molecules, under conditions which are so mild that, more particularly, optically active substances and biomolecules such as peptides, amino acids or nucleic acids can be used. Dipeptides having C-terminal glycines are not envisioned as desired substrates.

This problem is solved by combined use of an amidine base and a metal compound, more particularly during the transesterification, saponification or splitting of polymer-bonded molecules, e.g. in Merrifield synthesis. In the case where peptide esters were saponified, it was found that splitting could be brought about under mild conditions with lithium hydroxide alone, without the amidine base. We have unexpectedly found that use of an amidine base in combination with a metal salt accelerates transesterification, ammonolysis or saponification of the aforementioned acid derivatives so strongly that even sensitive acid derivatives can be successfully reacted under mild conditions, i.e. low temperatures and short reaction times.

For example, sensitive peptide esters can be transesterified or saponified without racemisation of the C-terminal amino acid on the α-C atom. There is no effect on any protected side-chain functional groups not containing an ester group. For example, a heptapeptide ester was quantitatively saponified with DBU/LiBr in $THF/H_2O$ in a short reaction time and without racemisation. On the other hand, saponification with aqueous NaOH was accompanied by some decomposition and resulted in racemisation.

It is also unexpectedly possible, by the method according to the invention, to convert simple esters such as methyl ester into complex esters such as menthyl ester.

DETAILED DESCRIPTION OF THE INVENTION

Conventionally peptides and polynucleotides are synthesized on polymer carriers by novel techniques (Merrifield synthesis). The link with the polymer carrier is usually an ester or amide bond. The carrier material often has to be split off under drastic reaction conditions, usually resulting in loss of all the protective groups of any protected functional groups in the peptide or polynucleotide. Trifluoroacetic acid/HBr/TMS (trifluoromethane sulphonate) HF/anisole, $NaOH/dioxane/H_2O_2$ or dimethyl aminoethanol/thallium ethanolate are examples of conventional splitting reagents. In contrast to these drastic conditions, the combination of an amidine base and a metal salt, particularly a lithium salt, constitutes an excellent reagent for splitting the bond between a peptide or polynucleotide and the polymer carrier. As a result of splitting, esters, amides or the corresponding free acids of the peptide or polynucleotide can be obtained as required, without decomposition or racemisation.

There is no effect on the non base labile protective groups of any other functional groups in the molecule. This method is particularly suitable for liberating sensitive molecules and for producing protected peptide segments on the polymer carrier as required for subsequent segment coupling to longer peptide chains. One particular advantage is that there is no need for sensitive and sometimes dangerous reagents such as HF or TlOEt.

Usually, the acid derivatives are transesterified by the method according to the invention as follows:

The ester is dissolved or suspended in an alcohol, optionally with addition of another solvent such as THF or $CH_2Cl_2$. After adding the amidine base, e.g. DBU or DBN in a 0.01–10 molar proportion, preferably in a 0.2–4 molar proportion, and after adding the metal compound, preferably salts of magnesium or caesium and particularly preferably lithium in a 0.1–20 molar proportion, more particularly in a 2–10 molar proportion, the reaction is brought about at temperatures between −30° C. and 120° C., preferably temperatures between −20° C. and 65° C. In the case of esters sensitive to racemisation, the preferred temperatures are between −20° C. and 30° C. for short reaction times (the minimum necessary).

When esters of low alcohols are transesterified with more complex alcohols it may be advantageous to distill off the lower alcohol evolved during the reaction.

Usually the acid derivatives, preferably an ester, are saponified by the method according to the invention as follows:

The acid derivative is dissolved or suspended in a solvent, preferably ethers such as THF or dioxane. After adding water (1+, preferably 10–100-fold molar proportion), the amidine base, e.g. DBU or DBN, used in a 1–10 molar proportion, preferably a 1–4 molar proportion, and adding the metal compound, preferably salts of lithium, magnesium or caesium in 0.1–20 molar proportion, particularly in 2–10 molar proportion, the reaction is brought about at temperatures between −20° and 65° C. The sequence of additions is arbitrary. Derivatives sensitive to racemisation are preferably reacted at between −20° C. and 30° C. for short reaction times.

The metal compounds in the aforementioned method are preferably halides, particularly a bromide or chloride, or a hydroxide (specially for saponification), perchlorate, acetate, sulphate or carbonate. The alcoholates of metal compounds are also suitable for trans-esterification or alcoholysis reactions.

For the purpose of ammonolysis of a carboxylic acid ester, preferably an amino acid or peptide ester, the ester is dissolved or suspended in a polar solvent, more particularly THF or dioxane, to which some DMF (up to 30 vol. %) can be added. The amidine base and the metal compound, preferably a lithium salt, a palladium salt, a copper (I) compound as the anion halides and perchlorate are particularly suitable) are added and NH3 is introduced with cooling. LiBr, $LiClO_4$, KF, CuCl or $PdCl_2$ are particularly suitable metal compounds, and these salts, more particularly KF, can be introduced on $Al_2O_3$ into the reaction mixture.

Amidine bases are organic compounds containing the structural element

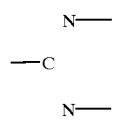

the free valencies of the nitrogen atoms being bonded to hydrogen and preferably (more particularly all) being bonded to carbon atoms. The free valency on the carbon atom is preferably bonded to an additional carbon atom, or alternatively to an additional nitrogen atom.

The amidine bases are preferably non-nucleophilic tertiary bases. The following bicyclic compounds are particularly suitable:
1,8-diazabicyclo[5,4,0]undec-7-ene (DBU) or 1,5-diazabicyclo[4.3.0]non-5-ene (DBN). The amidine base is normally used in a 0.01–10 molar proportion relative to the acid derivative. The best results are obtained with 0.2–4 molar proportions. During saponification of esters a free acid group is produced, and consequently the amidine base must be used in at least a molar proportion, unless the acid group is trapped by an additional auxiliary base, preferably a tertiary amine such as triethyl amine. The auxiliary base can also be present in a buffer system.

The metal compound, particularly advantageously lithium or magnesium or caesium salts, is usually used in a 0.1 20 molar proportion. 2–10 molar proportions of the metal compound are particularly advantageous, in each case relative to the acid derivative.

The research leading to the present invention also showed that in some cases lithium hydroxide alone, or another lithium salt and a base (i.e. so that lithium and hydroxide ions are present in the reaction solution) can be used to saponify amino acid or peptide esters. A 1.0–20 molar proportion of lithium hydroxide is suitable, or preferably a 2–20 molar proportion of lithium hydroxide, relative to the compound to be saponified. If the lithium hydroxide is in a buffer system or if an auxiliary base is added, the lithium compound can also be added in a 0.1 molar proportion. The resulting free acid is then neutralized by the auxiliary base and the buffer system, so that the reaction solution for saponification retains its alkaline character.

The invention will be explained in detail with reference to the following examples.

General Instructions for Transesterifying Carboxylic Acid Esters

A: LiBr (5 eq.) and the corresponding carboxylic acid ester (1 eq.) are dissolved or suspended under dry argon in a suitable quantity of the desired absolute alcohol, giving a concentration of 0.2 to 0.3 M. Freshly distilled DBU (0.5 eq.) is added and the solution is agitated at room temperature. The course of the reaction is followed by thin-layer chromatography or gas chromatography. As soon as the reaction ceases, the reaction mixture is concentrated in a rotary evaporator in vacuo and hydrolysed with saturated aqueous $NH_4Cl$ or a 1 N HCl solution. The product is shaken out twice with diethyl ether, the combined organic fractions are washed with brine until the reaction is neutral, and are then dried over $Na_2SO_4$. After removal of the solvent in vacuo, the raw product is purified by distillation or flash chromatography.

B: In the case of expensive alcohols, LiBr, the corresponding methyl ester and a stoichiometric or slightly super-stoichiometric quantity of the alcohol (1–2 eq.) is dissolved in a mixture of tetrahydro-furan/methylene chloride (3:1 v/v) as per method A.

The reaction mixture is then reflux-heated under dry argon, and the released methanol is trapped in a 5 A molecular sieve disposed in a dropping funnel or an extractor between the reaction flask and the reflux condenser. The course of the reaction is followed as in method A, and the processing is similar.

General Method of Processing Peptide Esters

The reaction mixture is added to 200 ml ethyl acetate (150 ml ethyl acetate in a second separating funnel), and the extract is washed successively with 100 ml of 1 N HCl, 50 ml 1 N HCl, 100 ml 1 M $KHCO_3$, 50 ml 1 M $KHCO_3$ and twice with 50 ml $H_2O$, and is then dried over $MgSO_4$ and concentrated in vacuo. The residue is dried at reduced pressure for a number of hours.

EXAMPLE 1

Transesterification of Phenylacetic Acid Methyl Ester to Phenylacetic Acid Ethyl Ester Following method A, phenylacetic acid methyl ester (4.51 g, 30 mmol) and LiBr (13.03 g, 150 mmol) were dissolved in ethanol (150 ml). DBU (2.28 g, 15 mmol) was added and the reaction mixture was agitated at room temperature for an hour. It was then hydrolysed and processed as described. Vacuum distillation yielded 4.40 g (90% of the theoretical yield) of pure phenylacetic acid ethyl ester, b.p. 65.5–66° C./1 Torr.

EXAMPLE 2

Transesterification of phenylacetic acid methyl ester to phenylacetic acid-(R) menthyl ester Following method B, phenylacetic acid methyl ester (751 mg, 5 mmol), LiBr (2.17 g, 25 mmol) and (R)-(–)-menthol (751 mg, 5 mmol) were dissolved in $THF/CH_2Cl_2$ (3:1 v/v, 20 ml). DBU (0.37 ml, 2.5 mmol) was added and the reaction mixture was heated at reflux for several hours. The thin-layer chromatogram ($SiO_2$:pentane/diethyl ether 4:1 v/v) showed that transesterification was not complete after boiling at reflux for 24 hours. Even so, the reaction mixture was hydrolysed and processed. Flash chromatography ($SiO_2$ pentane diethyl ether 4:1 v/v) showed 691 mg (a 50% yield) of phenylacetic acid-(R)-menthyl ester in the form of an oil substantially pure in 1H-NMR.

EXAMPLE 3

Transesterification of phenylacetic acid methyl ester to phenylacetic Acid-2-trimethyl silyl thyl Ester Following method B, phenylacetic acid methyl ester (751 mg, 5 mmol) was transesterified with reflux with 2-trimethyl silyl ethanol (1.18 g, 1.43 ml, 10 mmol) in $THF/CH_2Cl_2$ (3:1 v/v, 20 ml). After refluxing for 8 hours, the reaction mixture was hydrolysed and processed. In the gas chromatogram and 1H-NMR the raw product, obtained in a quantitative yield, was shown to be substantially pure (<99% in the GC).

EXAMPLE 4

Preparation of R-(4RS, 5SR)-5-isopropyl-2-oxazolidinone-4carboxylic acid ethyl ester (3b)

R-(4SR, 5RS, 8SR)-1-aza-3,7-dioxa-4-(2'-propyl)-8-(tert.-butyl)-bicyclo[3.3.0]-octane-2,6-dione (302 mg, 1.25 mmol) and LiBr (543 mg, 6.25 mmol) were dissolved in ethanol (30 ml). DBU (0.37 ml, 2.5 mmol) was added and the resulting solution was agitated at room temperature for 2 hours. After acid hydrolysis, usual processing and flash chromatography ($SiO_2$: $CH_2Cl_2$/ethyl acetate 4:1 v/v), 192 mg (a 76% yield) of 3b was obtained in the form of a colorless viscous oil.

EXAMPLE 5

Preparation of Boc-Phe-Ala-OEt

After dissolving Boc-Phe-Ala-OMe (701 mg, 2 mmol) and LiBr (869 mg, 10 mmol) in ethanol (10 ml), DBU (150 µl, 1 mmol) was added at room temperature. After 6 minutes the reaction solution was treated with 1 N HCl (3 ml) and processed as previously described.

Yield: 700 mg (96%) with 2% starting product (1H-NMR) and a D-Ala content of 4% (GC).

EXAMPLE 6

Preparation of Boc-Phe-Ala-OCHMe$_2$

After dissolving Boc-Phe-Ala-OMe (701 mg, 2 mmol) and LiBr (869 mg, 10 mmol) in isopropanol (10 ml), DBU (150 µ, 1 mmol) was added at −10° C. After agitation for 44 hours at the same temperature, the reaction mixture was treated with dilute HCl/diethyl ether (3 ml) and processed as previously described.

Yield: 664 mg (88%) with 4% starting product (1H-NMR) and a D-Ala content of 4% (GC).

EXAMPLE 7

Preparation of Boc-Phe-Ala-OCH$_2$ CH═CH$_2$(7d)

After dissolving Boc-Phe-Ala-OMe (701 mg, 2 mmol) and LiBr (869 mg, 10 mmol) in allyl alcohol (10 ml), DBU (150 µl, 1 mmol) was added at 0° C. After agitation at 0° C. for 6 hours, dilute HCl/diethyl ether (3 ml) was added to the reaction mixture and processed as described hereinbefore.

Yield: 686 mg (91%) of slightly brownish 7d with 3% of the starting product (1H-NMR) and a D-Ala content of 5% (GC).

EXAMPLE 8

Peptide-resin alcoholysis, Boc-Leu-Ala-Gly-Val-OMe (15b) (SEQ ID NO:1)

After suspending Boc-Leu-Ala-Gly-Val-(PS-Pam resin) (15a) (300 mg, 0.168 mmol peptide) in 3 ml of a 0.28 M LiBr/methanol solution (487 mg LiBr/20 ml methanol) and agitation at room temperature for 15 minutes, DBU (50 µl, 0.34 mmol) was added. After agitation at room temperature for 4 hours, the reaction mixture was filtered and the resin was washed with ethyl acetate (about 10 ml), treated with 1N HCl (about 10 ml) and twice extracted with ethyl acetate (about 10 ml). After drying the combined organic extracts with magnesium sulphate, filtering, evaporation of the solvent and drying in a high vacuum, 78 mg of 15b were obtained, slightly contaminated with a D-Val content of 1% (GC). Additional purification by flash chromatography (5% methanol in diethyl ether), after drying for 24 hours in a high vacuum, yielded 66 mg (83%) of 15b in the form of a white powder melting at 71–72° C.

EXAMPLE 9

Splitting of Peptide and Resin. Production of Boc-Leu-Ala-Gly-Val-OH (15c)

After suspension of Boc-Leu-Ala-Gly-Val-(PS-Pam resin) (15a) (150 mg, 0.093 mmol peptide) in a solution of LiBr (40 mg, 0.46 mmol) in THF (1.8 ml) and water (0.2 ml) and agitation for 15 minutes at room temperature, DBU (7 µl, 0.047 mmol) was added. After agitation at room temperature for 4 hours, the reaction mixture was filtered and the resin was washed with ethyl acetate (about 10 ml), treated with 1N HCl (about 10 ml) and extracted twice with ethyl acetate (about 10 ml). After drying the combined organic extracts with $MgSO_4$, filtering and distilling of the solvent, the mixture was dried in a high vacuum. The resulting product (81 mg) was slightly contaminated with a 1% content of D-Val (GC). The yield was determined by $_1$H-NMR on the crude product using acetonitrile as the internal standard and was 34 mg (81%). Esterification of the crude product with $CH_2N_2$ resulted in a product with a 1H-NMR spectrum corresponding to the spectrum of 15b.

EXAMPLE 10

Peptide Resin Alcoholysis. Boc-Leu-Ala-Glv-Phe-OMe (16b) (SEQ ID NO:2)

After suspension of Boc-Leu-Ala-Gly-Phe-(PS-Pam resin) (16a) (150 mg, 0.084 mmol peptide) in a solution of LiBr (36 mg, 0.41 mmol) in MeOH (2 ml) and after agitation for 15 minutes at 0° C., DBU (6.3 μl, 0.042 mmol) was added. After agitation at 0° C. for 8 hours, the reaction mixture was filtered and the resin was washed with ethyl acetate (about 10 ml), treated with 1N HCl (about 10 ml) and processed as before (half the quantity of solvent). The product was 64 mg of 16b, a colorless oil with a D-Phe content of 2% (GC). The content of 16b was 38 mg (86%) as determined by 1H-NMR on the crude product using acetonitrile as an internal standard. Further purification by flash chromatography (10% v/v MeOH/diethyl ether), after drying for 24 hours over a high vacuum, yielded 36 mg (82%) of 16b in the form of a white powder.

EXAMPLE 11
Peptide-resin Splitting. Production of Boc-Leu-Ala-Gly-Phe-OH (16c)

After suspension of Boc-Leu-Ala-Gly-Phe-(PH-Pam resin) (16a) (150 mg, 0.084 mmol peptide) in a solution of LiBr (36 mg, 0.41 mmol) in THF/10% v/v $H_2O$ (2 ml) and after agitation at room temperature for 15 minutes, DBU (6.3 μl, 0.042 mmol) was added. After agitation at room temperature for 4 hours, the reaction mixture was filtered and the resin was washed with ethyl acetate (about 10 ml), treated with 1N HCl (about 10 ml) and extracted twice with ethyl acetate (about 10 ml). After processing as before, 96 mg of impure 16c was isolated with a D-Phe content of 2% (GC). The content of 16c, measured over 1H-NMR on the crude product using acetonitrile as the internal standard, was 40 mg (93%). Esterification of the crude product with $CH_2N_2$ yielded a 1H-NMR spectrum corresponding to 16b.

EXAMPLE 12
Ac-D-Nal-D-p-Cl-Phe-D-Pal-Ser-Tyr-D-Cit-Leu-OH 250 mg (0.223 mmol) of Ac-D-Nal-D-p-Cl-Phe-D-Pal-Ser-Tyr-D-Cit-Leu-OMe was suspended in 15 ml of THF, the suspension was mixed with 1 ml water and a solution of 11.2 mg (0.468 mmol) LiOH in 1 ml water, and the reaction mixture was agitated at room temperature for 4 hours, after which the HPLC failed to show any more educt. The reaction solution was brought to pH 4 with 1N hydrochloric acid, the THF was removed in vacuo, and the residue was diluted with 15 ml water and suction-filtered. The product was digested with 30 ml acetonitrile while hot at 80° C. and again suction-filtered and dried. The final product was 220 mg (90%) of Ac-D-Nal-D-p-Cl-Phe-D-Pal-Ser-Tyr-D-Cit-Leu-OH, with 98.5% purity as per HPLC. The 1H-NMR spectrum did not contain the signal of the methyl ester at 3.6 ppm, but in other respects the spectrum was similar to a spectrum of Ac-D-Nal-D-p-Cl-Phe-D-Pal-Ser-Tyr-D-Cit-Leu-OH prepared independently for comparison. A GC racemate test showed no significant racemisation of leucine (D-Leu 0.5%).

EXAMPLE 13
Ammonolysis, Preparation of Boc-Phe-Ala-$NH_2$ 300 mg (0.86 mmol) of Boc-Phe-Ala-OMe and 274 mg (2.6 mmol, 3 eq) were dissolved in 30 ml dry THF and 400 mg KF were suspended on $Al_2O_3$ (approx. 2.2 mmol F.). A stream of dried $NH_3$ gas was sent through at 0° C. After 24 hours the educt had substantially been used up. 1H-NMR showed an ester content of about 10%. No side-products were shown in the DC.

EXAMPLE 14
(Comparative)—Preparation of Boc-Phe-Ala-OEt by Means of the Interesterification of Boc-Phe-Ala-OMe with $Ca(OAc)_2$ in Ethanol (method of Miranda et al. Int. J. Pep. Prot. Res. Vol. 37, (1991) pp. 451–6)

1.7 g calcium acetate were dissolved and suspended in 200 ml ethanol abs. After the addition of 0.7 g (2 mmoles) Boc-Phe-Ala-OMe the mixture was agitated 2 days at room temperature. After this time only educt was able to be demonstrated in the HPLC. Even after several hours of agitation at 40° C. no conversion (reaction) was able to be observed. The solvent was removed in a vacuum and the residue taken up in 100 ml ethyl acetate and 100 ml water. The ethyl acetate phase was washed successively with 50 ml of a saturated, aqueous $NaHCO_3$ solution and a saturated, aqueous NaCl solution and dried with sodium sulfate. After the removal of the sodium sulfate by suction the solvent was removed in a vacuum and the residue dried in an oil pump vacuum. Finally, 0.7 g of a solid was obtained which was, according to $^1$H-NMR, the educt used.

In contrast thereto, the interesterification of Boc-Phe-Ala-OMe to the corresponding diethyl ester according to the method of Seebach succeeds in a 96% yield (example 5 of the U.S. application).

Comparative example 1 demonstrates that the method of Miranda doesn't work at all by a transesterification reaction of Boo-Phe-Ale-OMe with $Ca(OAc)_2$. In contrast, our claimed method yields 96% of the desired product (example 5 of the above-identified patent application).

EXAMPLE 15

(Comparative)—Preparation of Z-Asn-Leu-1 Ome by Means of the Interesterification of Z-1-ASM-Leu-OEt with DBU/LiBr in Methanol (Seebach method) Seebach et al. Helv. Chim. Actu. Vol. 74 (1991) pp 1102–1118

0.81 g (2 mmoles) Z-Asn-Leu-OEt were dissolved in 25 ml anhydrous methanol. After the mixture cooled down to 0° C. 0.87 g (10 mmoles) LiBr and 0.15 ml DBU were added and the mixture agitated at this temperature overnight. According to HPLC no more educt was present after this time. After the addition of 1 ml in HCl the solvent was removed in a vacuum and the oily residue digested until complete crystallization with 100 ml water. The product was removed by suction and dried in an oil pump vacuum. Finally, 0.58 g (73.4%) of a white powder accumulated which was, according to $^1$H-NMR, the interesterification product Z-Asn-Leu-OMe. The diethyl ester was not able to be demonstrated any more in either the HPLC or in the $^1$H-NMR. According to a gas-chromatographic racemate test the portion of D-leucine in the product was 1% (educt 0.45%), that is, only a very slight racemization took place under the reaction conditions.

In contrast thereto, only 13% of the methyl ester was produced with the method of Miranda (calcium acetate, methanol, 35° C., 24 h reaction time) (no statement about the racemization).

Comparative example 2 shows the superiority of our method with clearly higher yields (73.4% vs. 13%) than the method of Miranda. Additionally, we find nearly no racemization.

What is claimed is:

1. A method for preparing peptides, peptide esters, amino acids or amino acid esters, optionally bonded to a polymer, wherein when the peptide is a dipeptide it does not include a C-terminal glycine, comprising reacting peptide ester or amino acid ester starting material, which contains a chiral carbon at the alpha position carbon, in solution under transesterifying or saponifying conditions with a member of the group consisting of alcohols and water in the presence of an amidine base and an alkali metal compound from group 1A of the Periodic table of the elements, at a temperature of up to 30° C.

2. The method of claim 1, further including a step of adding a solvent selected from the group consisting of an alcohol, tetrahydrofuran, methylene chloride, dioxane, toluene and mixtures thereof.

3. The method of claim 1, wherein the alkali metal compound is a lithium or a caesium compound.

4. The method of claim 1, wherein the alkali metal compound is a halide, perchlorate, acetate, sulphate or carbonate.

5. The method of claim 1, wherein the amidine base is an N-substituted non-nucleophilic amidine base.

6. The method of claim 5, wherein the amidine base is 1,8-diazabicyclo[5,4,0]-undec-7-ene (DBU) or 1,5-diazabicyclo[4,3,0]non-5-ene (DBN).

7. The method of claim 1, wherein the carboxylic acid ester is a peptide or amino acid optionally bonded to a polymer.

8. The method of claim 1, wherein the amidine base is used in a 0.01 to 10 molar proportion with respect to the ester.

9. The method of claim 8, wherein the amidine base is used in a 0.2 to 4 molar proportion.

10. The method of claim 1, wherein the reaction occurs with water and consists of saponification to a free acid, and the amidine base is introduced in at least a molar proportion or the amidine base is introduced together with an auxiliary base in at least a molar proportion.

11. A method for preparing peptides, peptide esters, amino acids or amino acid esters, optionally bonded to a polymer, wherein when the peptide is a dipeptide it does not include a C-terminal glycine, comprising reacting a peptide ester or amino acid ester starting material, which contains a chiral carbon at the alpha position carbon, in solution under transesterifying or saponifying conditions with a member of the group consisting of alcohols and water in the presence of an amidine base and a lithium or caesium metal compound, at a temperature of up to 30° C.

12. A method for preparing peptides, peptide esters, amino acids or amino acid esters, optionally bonded to a polymer, wherein when the peptide is a dipeptide it does not include a C-terminal glycine, comprising reacting peptide ester or amino acid ester starting material, which contains a chiral carbon at the alpha position carbon, in solution under transesterifying or saponifying conditions with a member of the group consisting of alcohols and water in the presence of an amidine base and an alkali metal compound from group 1A of the Periodic table of the elements, at a temperature of up to 30° C. without causing racemization of the peptide ester or amino acid ester starting material.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Leu Ala Gly Val
1

(2) INFORMATION FOR SEQ ID NO:2:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Leu Ala Gly Phe